(12) United States Patent
Gregory (10) Patent No.: US 10,785,963 B2
(45) Date of Patent: Sep. 29, 2020

(54) METHOD OF GROWING SHELLFISH

(71) Applicant: Aqua Mould Systems NZ Limited, Kerikeri, Northland (NZ)

(72) Inventor: Shaun Gregory, Kaeo (NZ)

(73) Assignee: Aqua Mould Systems NZ Limited (NZ)

( * ) Notice: Subject to any disclaimer, the term of this patent is extended or adjusted under 35 U.S.C. 154(b) by 454 days.

(21) Appl. No.: 15/858,047

(22) Filed: Dec. 29, 2017

(65) Prior Publication Data

US 2018/0184625 A1 Jul. 5, 2018

Related U.S. Application Data

(63) Continuation-in-part of application No. 14/400,823, filed as application No. PCT/NZ2013/000089 on May 28, 2013, now abandoned.

(30) Foreign Application Priority Data

May 29, 2012 (NZ) .......................... 600311

(51) Int. Cl.
*A01K 61/00* (2017.01)
*A01K 61/50* (2017.01)
*A01K 61/54* (2017.01)
*A01K 61/55* (2017.01)
*A01K 61/90* (2017.01)
*A01K 67/00* (2006.01)
*A01K 67/033* (2006.01)

(52) U.S. Cl.
CPC .............. *A01K 61/54* (2017.01); *A01K 61/00* (2013.01); *A01K 61/50* (2017.01); *A01K 61/55* (2017.01); *A01K 61/90* (2017.01); *A01K 67/00* (2013.01); *A01K 67/033* (2013.01); *Y02A 40/81* (2018.01)

(58) Field of Classification Search
CPC ......... A01K 61/54; A01K 61/55; A01K 61/50
USPC ......................... 119/234, 236, 238, 239, 240
See application file for complete search history.

(56) References Cited

U.S. PATENT DOCUMENTS

| | | | | |
|---|---|---|---|---|
| 3,750,625 A | * | 8/1973 | Edwards | .............. A01K 67/033 |
| | | | | 119/6.6 |
| 4,317,429 A | * | 3/1982 | Leighton | ................ A01K 61/54 |
| | | | | 119/241 |
| 2010/0294203 A1 | * | 11/2010 | Janke | ..................... A01K 61/54 |
| | | | | 119/236 |

* cited by examiner

Primary Examiner — Christopher D Hutchens
Assistant Examiner — Steven J Shur
(74) Attorney, Agent, or Firm — Gloria Tsui-Yip, Esq.; Gottlieb, Rackman & Reisman, P.C.

(57) ABSTRACT

A method of growing shellfish is disclosed. The method comprises obtaining a support tray (I) with recesses (7) where at least some of the recesses (7) incorporate means adapted to create a deliberately formed alphanumeric, written or pictorial mark on the shellfish as it grows. Shellfish spat are attached to at least some of the recesses (7) and the tray (I) is placed in water so that the spat grow into substantially mature shellfish within the recesses (7). The spat each grow generally in the shape of their respective recess (7) so that the mark is created on the shellfish as it grows.

10 Claims, 7 Drawing Sheets

Fig.5

METHOD OF GROWING SHELLFISH

FIELD OF INVENTION

This invention relates to a method of growing shellfish, for example oysters.

BACKGROUND

It is known to grow oysters using ropes, racks or baskets. Equipment and oysters can be damaged by exposure to the elements when using existing methods of growing oysters in the ocean. It is accordingly an object of a preferred form of the invention to go at least some way towards addressing this problem or to at least provide the public with a useful choice.

The term "comprising" and derivatives thereof, eg "comprises", if and when used herein in relation to a combination of features should not be taken as excluding the possibility that the combination may have further unspecified features. For example, a statement that an arrangement "comprises" certain parts does not mean that it cannot also, optionally, have additional parts.

SUMMARY OF INVENTION

According to one aspect of the invention there is provided a method of growing shellfish comprising the steps of:
 a) taking a support having a plurality of recesses wherein at least some of the recesses incorporate means adapted to create a deliberately formed alphanumeric, written or pictorial mark on the shellfish as it grows;
 b) attaching shellfish spat to at least some of the recesses respectively; and
 c) placing the support in water such that the spat grow into substantially mature shellfish within the recesses such that the shellfish are each generally in the shape of their respective recess and such that the mark is created on the shellfish as it grows.

Optionally the shellfish comprise oysters.

Optionally the oysters are removed from the support when they are substantially mature.

Optionally the support has one or more channels running between at least some of the recesses.

Optionally the support comprises a tray which has the recesses.

Optionally the recesses are arranged in rows.

Optionally each recess has at least one opening to the channel to allow air and water to enter and leave the recess by way of the channel.

Optionally the support has walls and corresponding spaces that enable the support to be stacked with other supports.

Optionally the means adapted to create the mark comprises a raised part within each corresponding recess.

Optionally the mark comprises a symbol.

According to a further aspect of the invention there is provided a shellfish when grown or growing according to the method set out above.

According to a further aspect of the invention there is provided a support for growing shellfish having a plurality of recesses arranged in a series of parallel rows wherein at least some of the recesses incorporate means adapted to create a deliberately formed alphanumeric, written or pictorial mark on the shellfish as it grows, each recess having at least one opening to a channel adapted to allow air and water to enter and leave the recess when the support is in use with shellfish growing.

Optionally the support is a tray with walls and corresponding spaces that enable the tray to be stacked with other similar trays.

BRIEF DESCRIPTION OF THE DRAWINGS

Some preferred forms of the invention will now be described by way of example and with reference to the accompanying drawings, of which.

DETAILED DESCRIPTION

Figure 1:
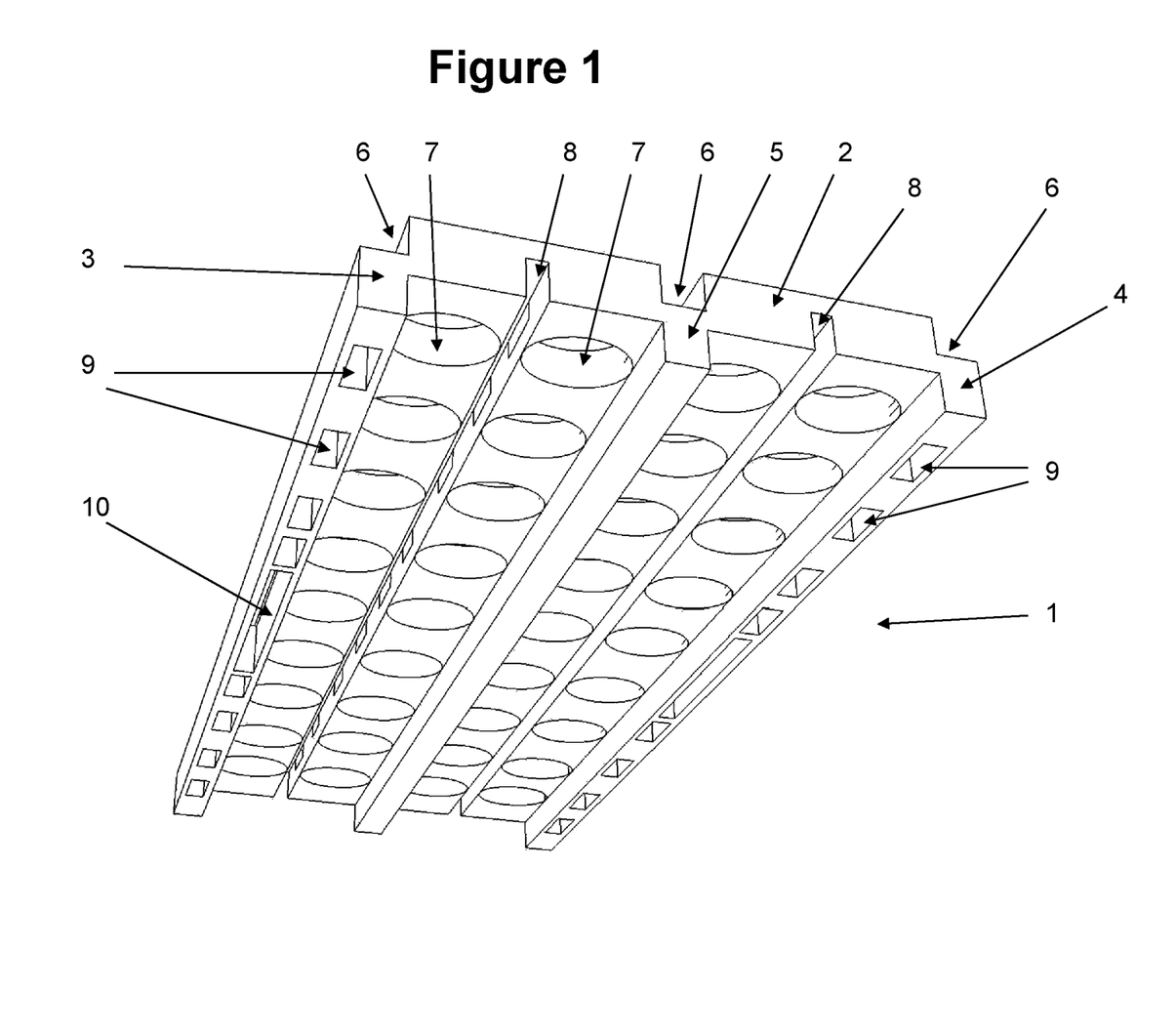
FIG. 1 is a perspective view of an oyster growing tray.

Referring to FIG. 1, a preferred embodiment of the invention comprises a tray 1 for use in growing oysters. The tray 1 has a body 2, outer walls 3, 4 and an inner wall 5. There are spaces 6 in the upper surface of the body 2 of the tray 1. The spaces 6 are complementary to the walls 3-5 and so enable the tray 1 to be stacked above or below other trays of the same design. The tray 1 is made from strong substantially inflexible plastic or other suitable material.

The tray is formed in two similar halves with the inner wall 5 running between each half. In each half there are two parallel rows of recesses 7. A channel 8 runs between the two rows of recesses 7 in each half of the tray 1. As can be seen clearly in FIG. 1, there are therefore in total four rows of recesses 7 and two channels 8 in the tray 1.

Figure 2:
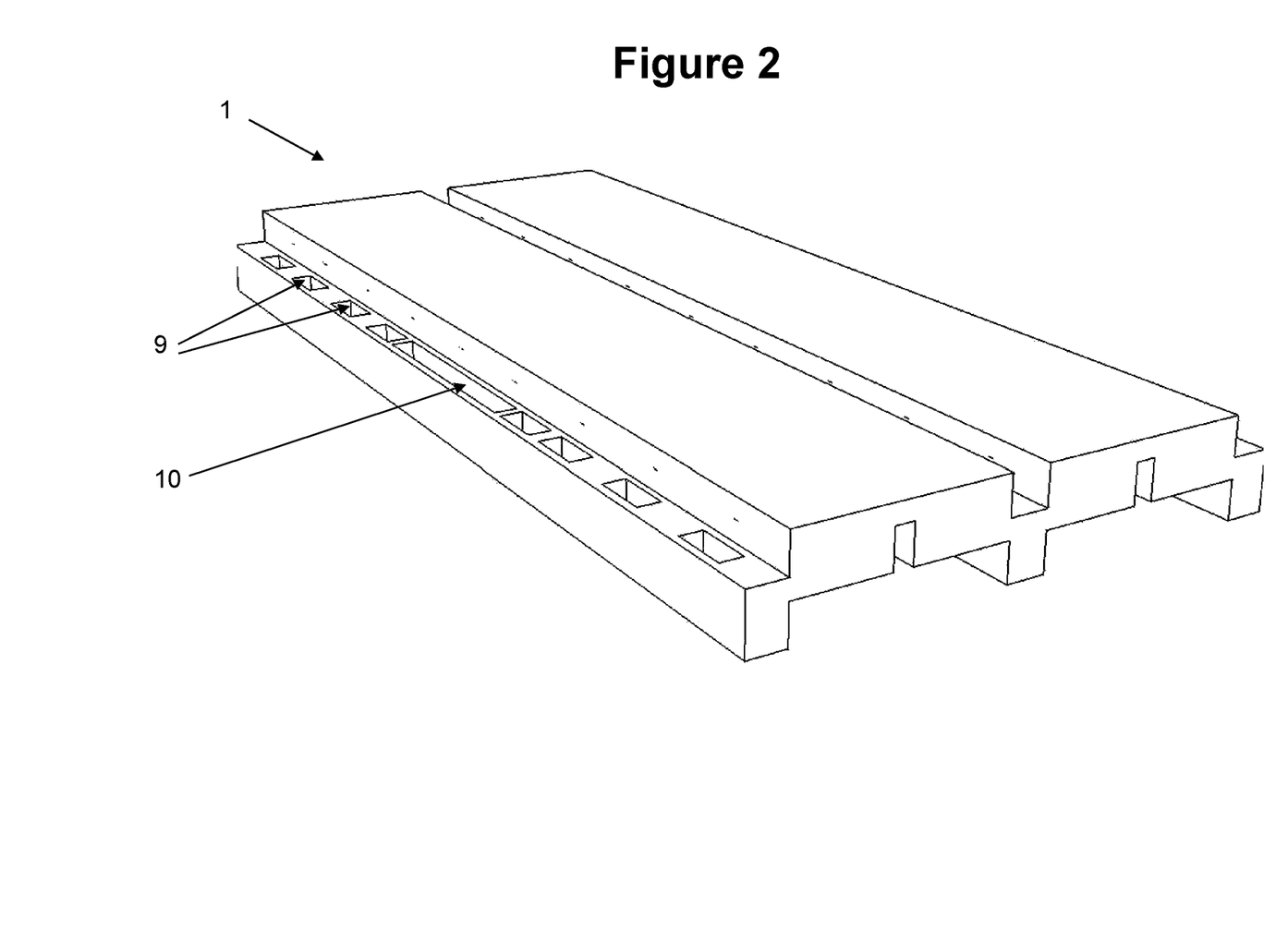
FIG. 2 is a top perspective view of the tray.

The outer walls 3, 4 have a number of peg apertures 9 for securing the tray 1 when in use, as described below. Each outer wall 3, 4 also has a handle aperture 10 to which a handle can be attached for securing the tray 1 when in use as an alternative to using pegs. FIG. 2 illustrates the peg apertures 9 and handle aperture 10 on one outer wall 3 of the tray 1.

Figure 3:
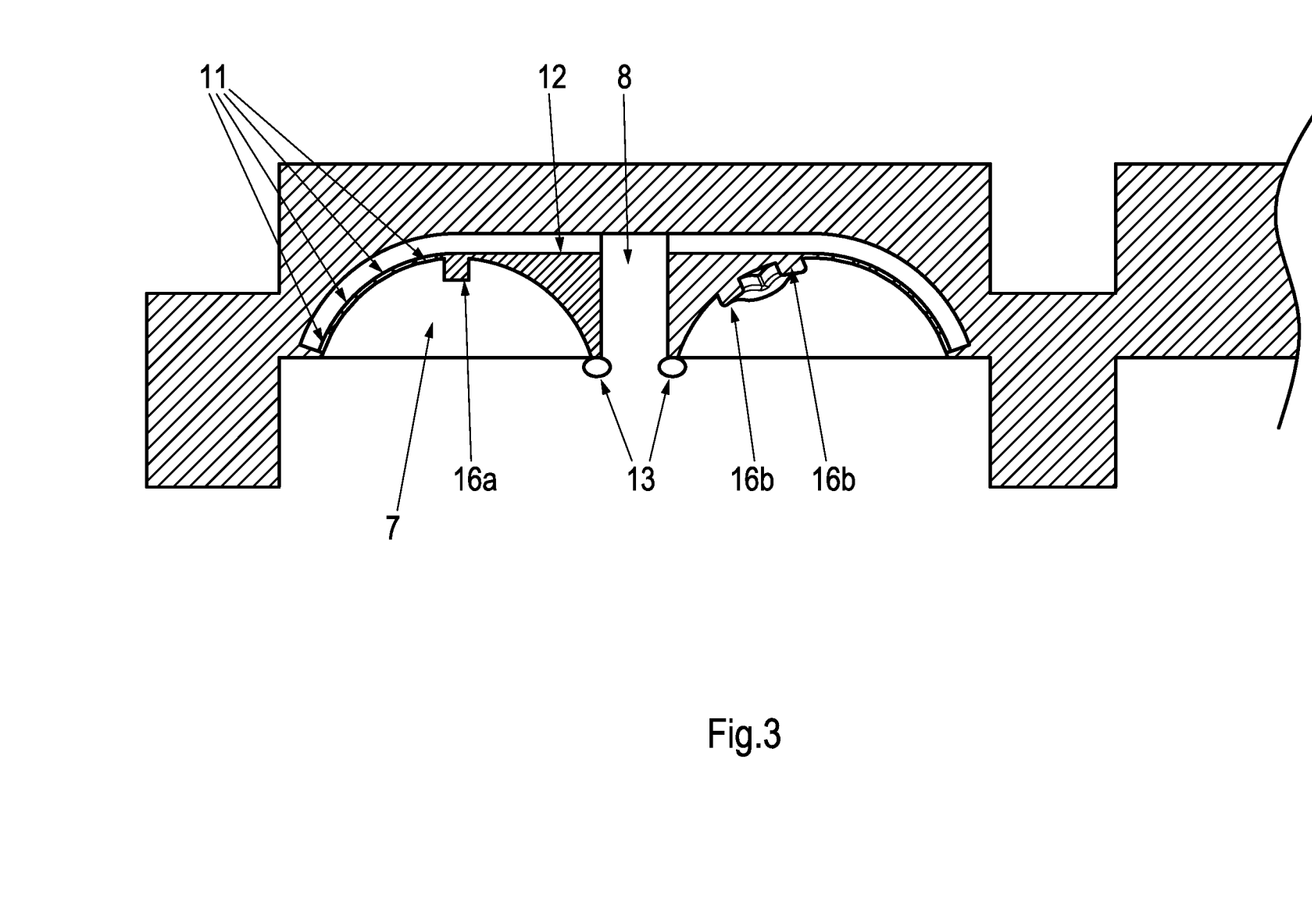
FIG. 3 is a, simplified, partial cross section view of the tray.

An oyster is grown in each recess 7 of the tray 1. As can be seen in FIG. 3, each recess 7 has a series of air holes 11 that connect the recess 7 to a conduit 12 that opens into the channel 8. When the tray 1 is in use to grow oysters, the first step is to glue an oyster spat 13 (e.g. a larva) to the edge of the recess 7 nearest the channel 8. The spat 13 may be bred or caught in the wild. The spat 13 will grow forward and so it is glued with its rear part at the edge of the recess with its front part pointing towards the recess 7 so that it grows into the recess. An ideal size for the spat 13 is approximately 2 cm long although larger or smaller spat can also be used. Over time the spat 13 will grow into and will eventually fill the space of the recess 7 to become a mature oyster. Once spat 13 has been glued at each recess 7 of the tray 1 the process is repeated with other trays until the desired number of trays is ready to be farmed. In an in-use growing disposition the trays are placed with the recesses 7 facing downward.

Oyster farming is traditionally carried out in one of a number of possible ways. Intertidal oyster farming may involve a series of horizontally-disposed ropes or wooden racks positioned in the ocean to which sticks, trays or bags are attached. The oyster spat 13 is glued directly to the sticks or placed loose in trays or bags. In inter-tidal farming the ropes or racks are positioned in a tidal area of the ocean. The sticks, trays or bags sit above the water at low tide and are under water at high tide. In subtidal oyster farming the oysters are attached to a rope in deeper water and remain entirely under water during their life cycle. The tray 1 of the present invention is suitable for use in existing oyster farming methods but in the preferred embodiment is used in inter-tidal oyster farming.

If the tray 1 is to be used with wooden racks then it is preferred to use one tray level. Alternatively several trays may be stacked and then secured to a rack with pegs by way of the peg apertures 9. In an alternative embodiment of the invention nails can be used rather than pegs to secure each tray 1. The nails are nailed into the horizontally-disposed wooden racks so the tray 1 can sit on top of the racks with the nails coming up through the peg apertures 9. The top of the nail then has a peg pushed on to stop the tray from moving or floating. When removing the trays the peg is lifted off the nail and the tray 1 is lifted off the rack.

The trays may also be hung from the racks. Where trays are hung purpose-built handles may be inserted in the handle apertures 10 and nylon may be attached to the handles at one end and at the other end to clips which fasten to the racks. Alternatively nylon may be attached directly to the peg apertures 9 or the handle apertures 10. This nylon/clip arrangement is also suitable for hanging trays from horizontally-disposed ropes in inter-tidal farming. In an alternative embodiment of the invention the trays 1 are attached to vertically-hanging ropes in sub-tidal oyster farming.

Once the spat 13 are glued to trays 1, and the trays 1 stacked and attached to racks or ropes the oysters are left in the ocean to mature. As the recesses 7 face downward, the walls 3-5 act to keep the body 2 of the bottom tray 1 above the wooden racks when used in a rack system. Oysters in the stacked trays above the bottom tray 1 will be protected by the tray beneath it and by the recesses 7 they are growing in.

Referring to FIG. 3, in the preferred embodiment the air holes 11 in each recess 7 allow water and air to pass in and out of the recess 7 by way of the conduit 12 to the channel 8 during normal tidal movement. Specifically, the air holes 11 allow air to be pushed out of the recess 7 at an upward angle by the rising tide. This ensures that there is no air in the recess 7 once the tide rises above the level of the recess so that the growing oyster is not out of the water longer than the low tide period.

Figure 3A:
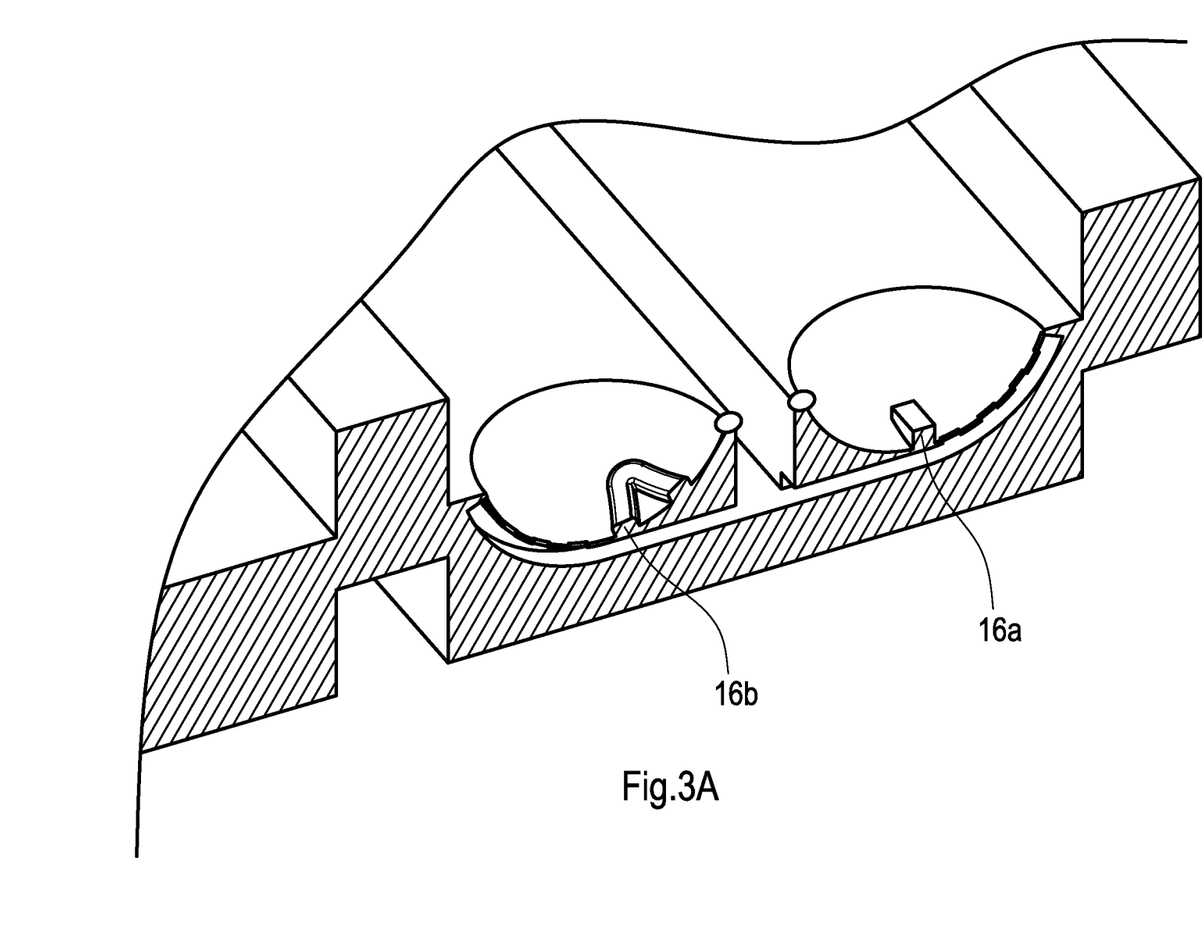
FIG. 3A is an upside-down perspective view of FIG. 3.
Figure 3B:
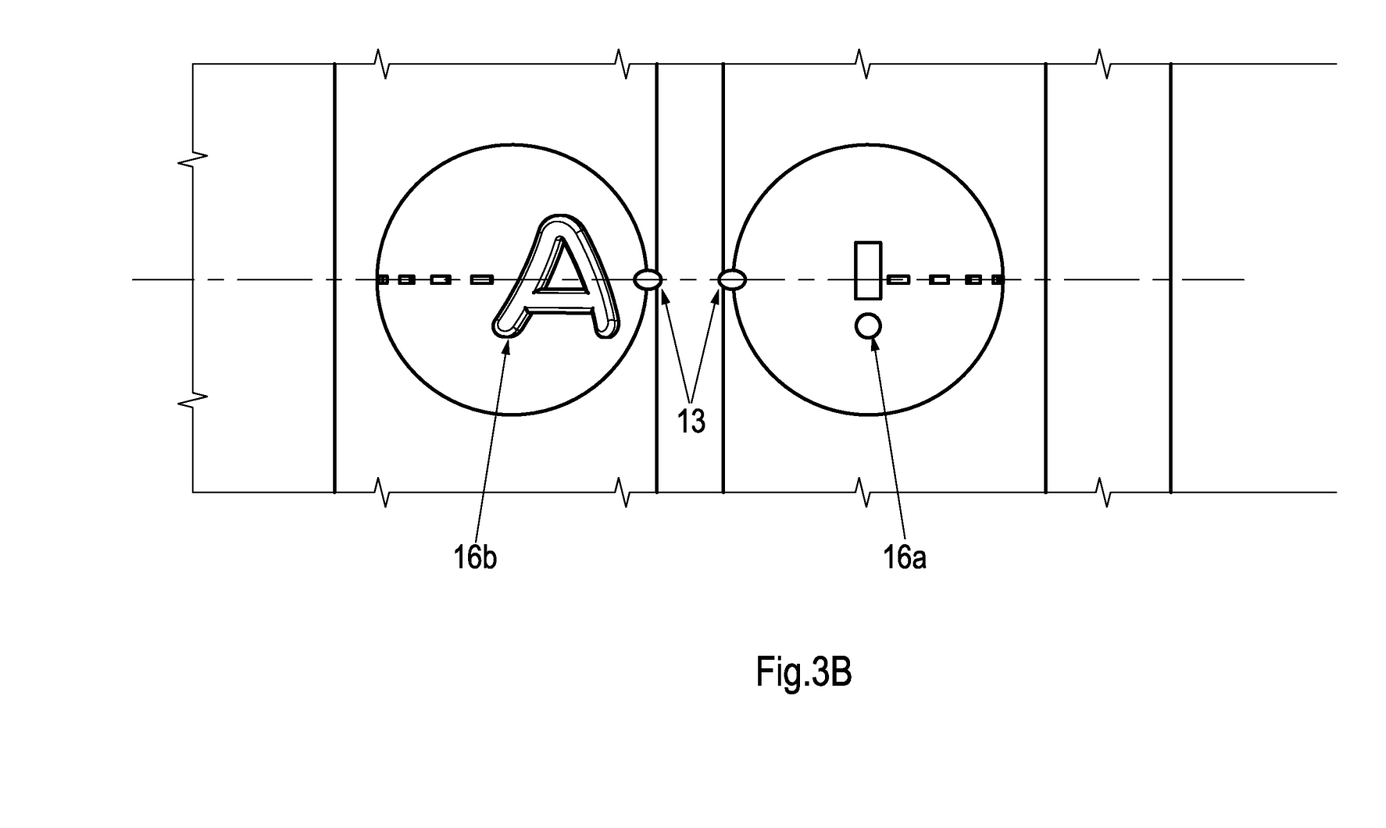
FIG. 3B is a top plan view of FIG. 3.
Figure 5:
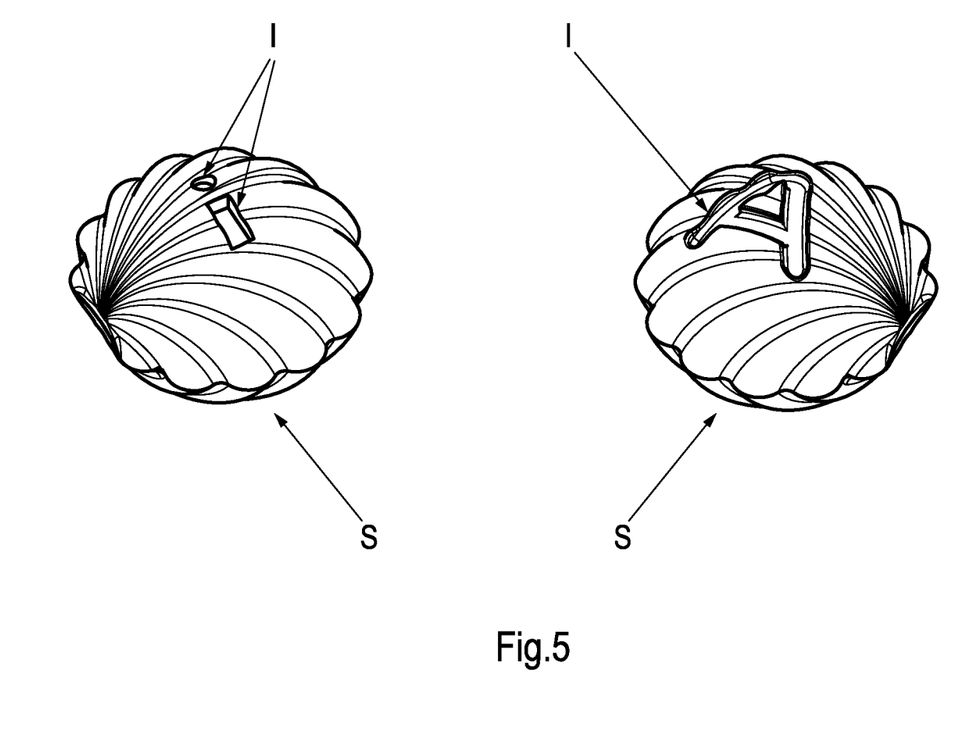
FIG. 5 is a perspective view of a shellfish with a corresponding indentation using the growing tray of the present invention.

As well as being protected within the recess 7, each oyster will tend to grow to substantially take the shape of the recess 7. The shape of the recess 7 shown in FIG. 1 is substantially cylindrical, whereas the shape of the recess 7 shown in FIG. 3 is hemispherical. Any shape recess 7, such as oval prism can be used to shape the oyster as desired. This means that oysters farmed using the tray 1 of the invention will be approximately the same size and shape, reducing the need to grade mature oysters. Trays 1 can be made in different sizes to produce different sized oysters. Use of trays 1 with recesses 7 also means that it is possible to brand the shell of each oyster by having a raised part, such as a raised word or shape 16, such as 16*a* or 16*b*, in each recess 7 or on the upper surface of the body 2 of the tray 1. The raised parts 16*a* and 16*b* as shown in FIG. 3 have, respectively, a rectangular cross-sectional shape (i.e. raised vertically) and a rounded edge or dome shape (i.e. not raised vertically). Any other cross-sectional shapes, uniform or non-uniform, regular or irregular, can be used for the raised part 16. The raised part 16*a* is shown to be positioned at the lowest, central, point of the recess 7, but the raised part 16 is not limited to be positioned at the lowest, central, point of the recess 7, as illustrated by raised part 16*b*. The raised part 16 can be positioned anywhere within the recess 7, and also can be positioned on the side of the recess 7 near where the spat 13 is attached. As illustrated in FIGS. 3A and 3B, raised part 16*a* is a rectangular shape (as part of the exclamation symbol or the lower case letter "i") and raised part 16*b* is the capital letter "A." As the shell grows into the shape of the recess 7 the raised word or shape 16 will be formed in the exterior of the shellfish S as a corresponding indentation I in the shell (see FIG. 5). Oysters can also be grown with a flat bottom allowing mature processed oysters to be free standing. When the shell has grown to the length and depth of the recess 7 it then continues to grow a thicker shell until it is ready to be processed. When the word "shape" is used in this application, it means any shape, whether geometric or irregular.

Once the oysters have matured the trays 1 are removed from the water, stacked on pallets and taken to a factory to be processed. The oysters are within the recesses 7 and this reduces the need to clean the oysters themselves and facilitates efficient cleaning of the trays 1. Each tray 1 is unstacked and placed on a conveyor belt with the side containing the mature oysters in the recesses 7 facing upward. Any over-catch i.e. spat settling onto exposed areas of the tray 1, is removed by compressed air. The conveyor belt passes beneath an air-knife opening machine (not shown). The machine opens the oysters by having a vibrating air-knife penetrate through the shell. It then cuts the muscle of each oyster releasing the bond between the top half and the bottom half of each shell. This top half of each shell is then removed. The oyster is now exposed in the lower half of its shell. If the oysters have been in a chiller for a certain period of time the flesh and shell can stick leading to tears of the flesh when the shell is removed. In this situation a jet of air or water may be directed by way of a jet situated on the blade of the air-knife.

Figure 4:
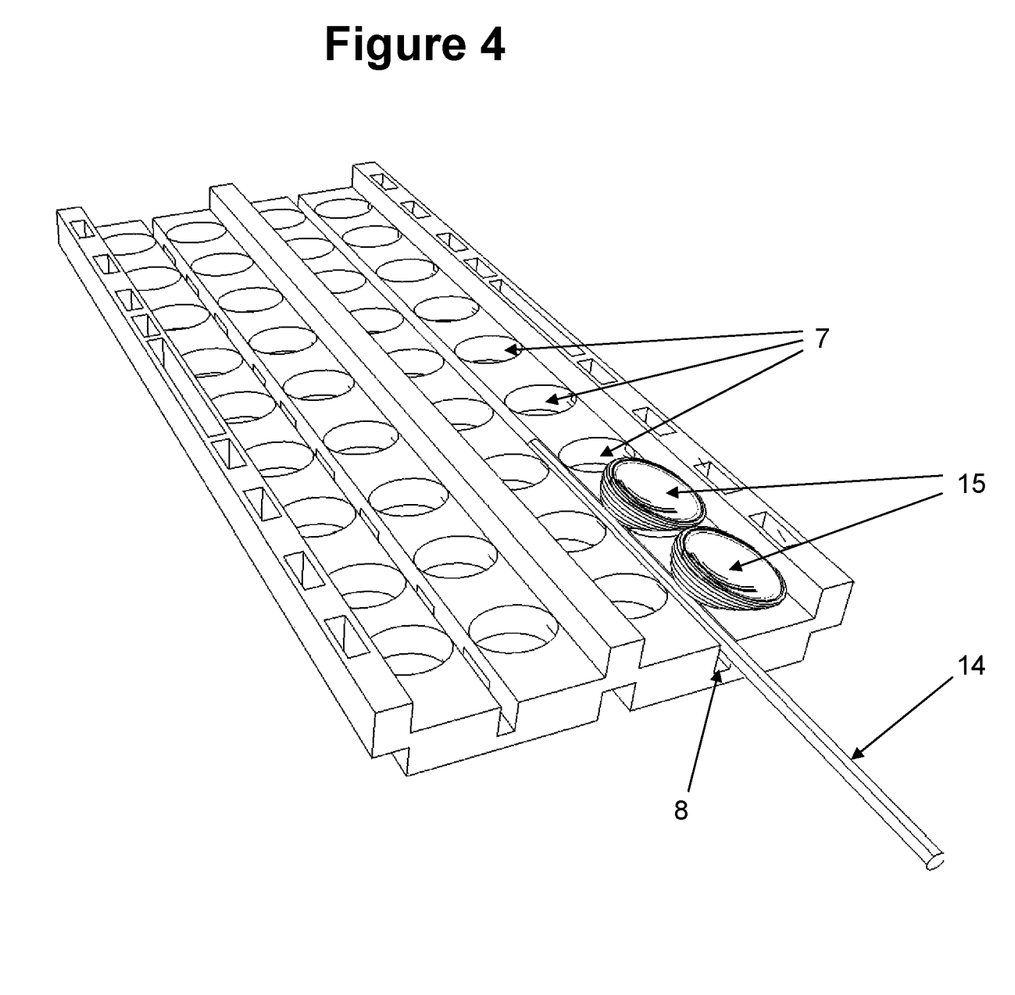
FIG. 4 is a perspective view of the tray in use during processing.

Referring to FIG. 4, further along the conveyor belt another machine directs a steel rod 14 through each channel 8 of each tray 1. As the steel rod moves through the channel 8 it contacts the rear end of a half-shelled oyster 15 and lifts the half-shelled oyster 15 out of the recess 7. Only one rod 14 and two half-shelled oysters 15 are shown in FIG. 4 but it should be appreciated that typically the tray 1 will contain half-shelled oysters 15 in all the recesses 7. The air holes 11 facilitate the lifting process by allowing air into the recess 7. The oysters are now removed from the tray 1 and packed into cartons ready for distribution. As the oysters grown using trays 1 are substantially the same size and shape as the recesses 7, the cartons can contain preformed dividers to hold oysters of that particular size and shape for convenient transport and to maximise use of space within the cartons.

While some preferred forms of the invention have been described by way of example it should be appreciated that modifications and improvements can occur without departing from the scope of the appended claims.

The invention claimed is:

1. A method of growing shellfish comprising the steps of:
    a) taking a support having a plurality of recesses, at least one channel connected with said plurality of recesses, and at least one conduit abutting each recess connected to said at least one channel to allow water and air to pass in and out of each recess, wherein at least one of the recesses has an upper open end and a lower recessed end, at least one opening on said lower recessed end connected to said conduit, and incorporates a raised part within the recess, such raised part creates a deliberately formed alphanumeric, written or pictorial corresponding indentation mark on the shellfish as it grows;

b) attaching shellfish spat adjacent to said upper open end of at least some of the recesses respectively; and c) placing the support in water such that the spat grow into substantially mature shellfish within the recesses;

d) growing the shellfish such that the shellfish are each generally in the shape of their respective recess and such that the indentation mark is created on the shellfish as it grows.

2. A method according to claim 1, wherein the shellfish comprise oysters.

3. A method according to claim 2, wherein the oysters are removed from the support when they are substantially mature.

4. A method according to claim 1, wherein said at least one channel is positioned between at least some of the recesses.

5. A method according to claim 1, wherein the support comprises a tray which has the recesses.

6. A method according to claim 1, wherein the recesses are arranged in rows.

7. A method according to claim 4, wherein air and water enter and leave the recess via said at least one opening, to said at least one conduit, to said at least one channel.

8. A method according to claim 1, wherein the support has walls and corresponding spaces that enable the support to be stacked with other supports.

9. A method according to claim 1, wherein the mark comprises a symbol.

10. A shellfish when grown or growing according to the method of claim 1.

* * * * *